United States Patent [19]

Simms et al.

[11] 4,159,639
[45] Jul. 3, 1979

[54] APPARATUS AND METHOD FOR MEASURING THE DEGREE OF REFINING OF PULP FIBERS IN THE PREPARATION OF FURNISH FOR PAPER MAKING

[75] Inventors: Romilly J. Simms, Menlo Park; Byron K. Madsen, Saratoga, both of Calif.

[73] Assignee: Ishikawajima-Harima Heavy Industries Co., Ltd., Tokyo, Japan

[21] Appl. No.: 852,817

[22] Filed: Nov. 18, 1977

[51] Int. Cl.² .......................................... G01N 15/04
[52] U.S. Cl. ........................................ 73/63; 73/61.4
[58] Field of Search ............... 73/63, 61.4, 61 R, 293, 73/60.1; 356/39, 208

[56] References Cited

U.S. PATENT DOCUMENTS

| | | |
|---|---|---|
| 2,346,945 | 4/1944 | Samson et al. ........................... 73/63 |
| 3,715,761 | 2/1973 | Drekter et al. .................. 356/208 X |
| 4,024,754 | 5/1977 | Alfthan ..................................... 73/63 |
| 4,041,502 | 8/1977 | Williams et al. ................. 73/61.4 X |

FOREIGN PATENT DOCUMENTS

| | | |
|---|---|---|
| 342574 | 10/1921 | Fed. Rep. of Germany .............. 73/63 |
| 2339696 | 2/1975 | Fed. Rep. of Germany ........... 73/61.4 |
| 1138862 | 6/1957 | France ....................................... 356/39 |
| 362639 | 2/1973 | U.S.S.R. ..................................... 73/63 |

*Primary Examiner*—S. Clement Swisher
*Assistant Examiner*—Joseph W. Roskos
*Attorney, Agent, or Firm*—Lowhurst & Aine

[57] ABSTRACT

An apparatus and a method for determining pulp quality by monitoring the rate of descent of the pulp-water interface of a uniformly intermixed stationary sample of pulp suspension, at a selected consistency, while it settles out.

11 Claims, 6 Drawing Figures

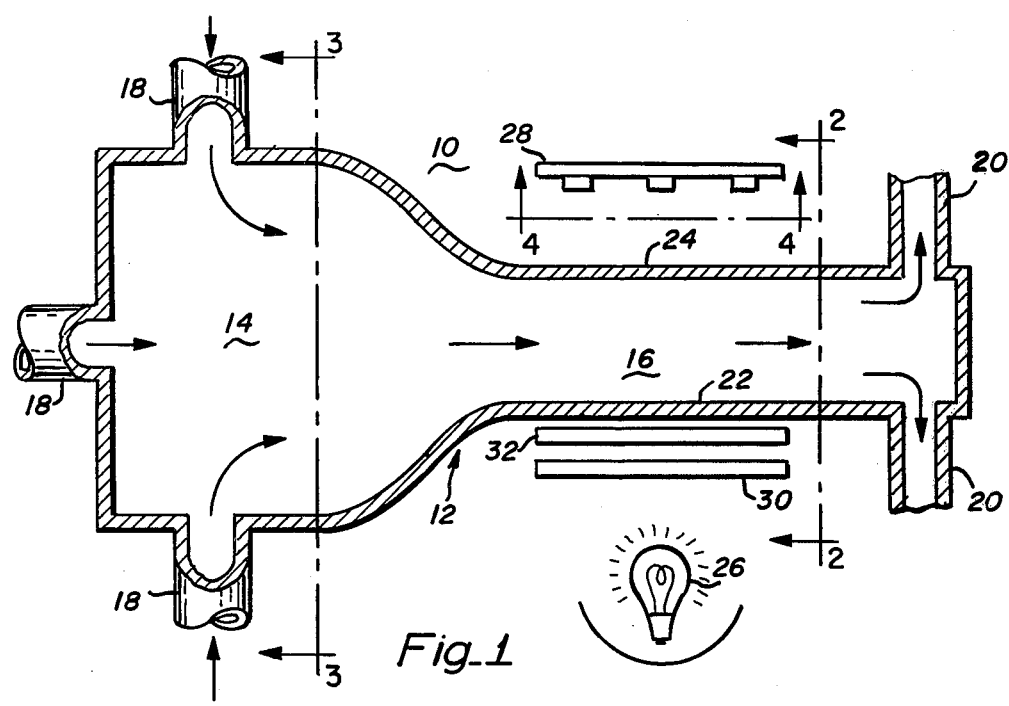
Fig_1
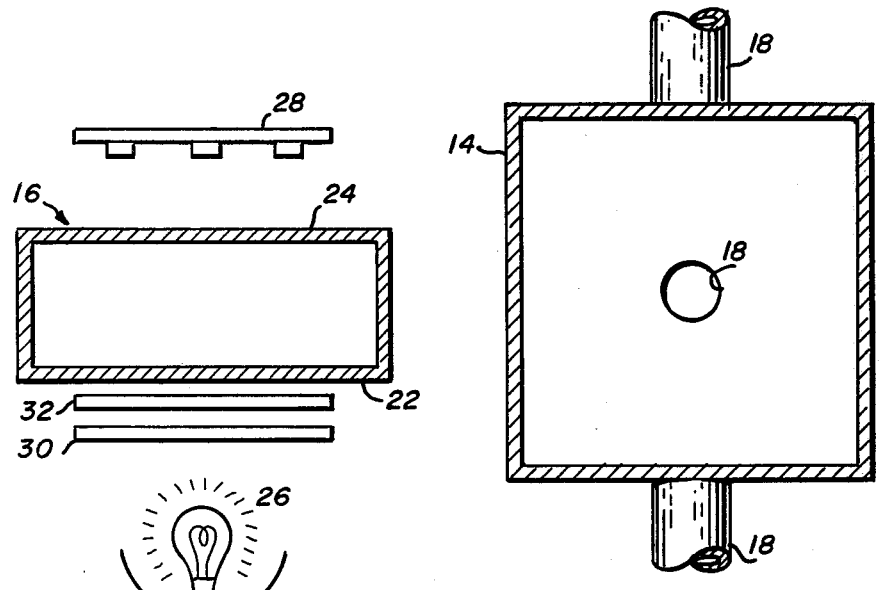
Fig_2
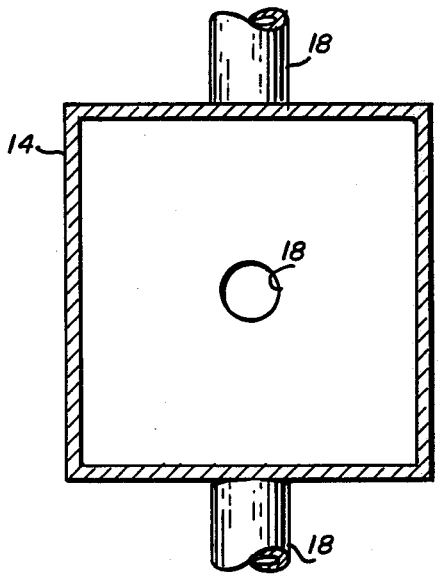
Fig_3
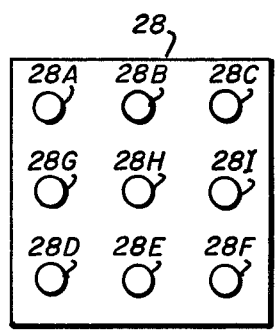
Fig_4

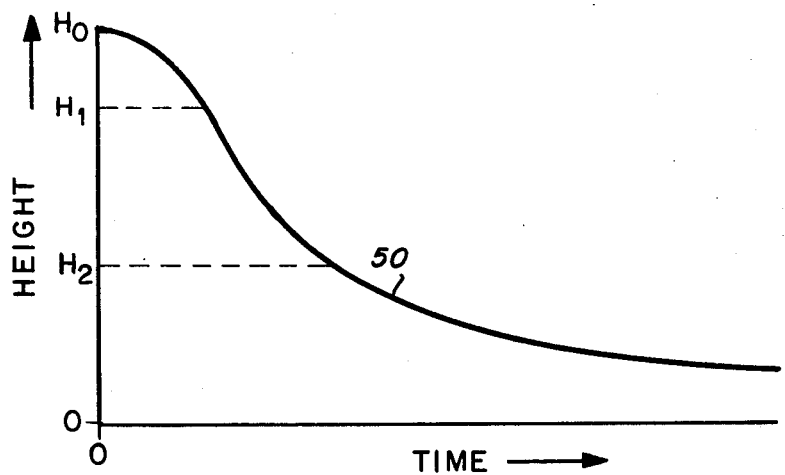
Fig_5
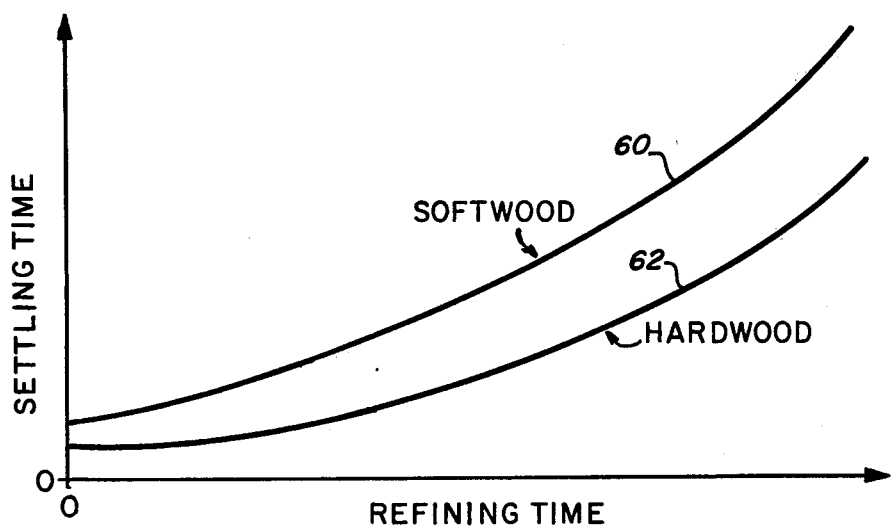
Fig_6

APPARATUS AND METHOD FOR MEASURING THE DEGREE OF REFINING OF PULP FIBERS IN THE PREPARATION OF FURNISH FOR PAPER MAKING

BACKGROUND OF THE INVENTION

This invention relates to an apparatus and a method for measuring the degree of refining of pulp fibers in a pulp suspension in the preparation of furnish for use in paper making, and more particularly to such a device and method for measuring certain properties of the pulp suspension, as modified by the refining process, to allow prediction of the physical properties of the to-be-manufactured paper.

In the making of paper, the fibers are produced by a pulping process which provides what is often referred to as either a stock preparation or a pulp suspension. In order to prepare such pulp suspension to generate a furnish, and in addition to such operations as repulping and blending of pulps of different types and the addition of various chemicals and fillers, it has been found that a mechanical treatment is necessary to make the fibers suitable for forming into sheets of paper. This mechanical treatment is referred to as refining. The refining process is fully described in chapter 4 of the second edition of volume III entitled "Papermaking and Paperboard Making" of a three volume work entitled "Pulp and Paper Manufacture."

One of the common methods heretofore employed to measure the degree of refining to which a pulp suspension has been subjected is the use of the freeness test which is based on the rate at which water would drain from a pulp suspension through a wire mesh on which the fibers are retained in the form of a loose fiber mat. It was found that the longer the pulp suspension was refined, the slower the water drained through the fiber mat. The main value of a freeness test lies in the relationship which the paper makers have found between this test taken on a stock prepared in their equipment and the behavior and characteristics of the sheet-forming process on a paper machine.

One of the disadvantages of the freeness test is that it is strongly influenced by the presence and concentration of fines, less so by the physical condition of the fibers. Consequently, correlation between the freeness test and the physical properties of the paper are greatly dependent on the fines present in the pulp suspension and since the fines do not add materially to the physical properties of the paper, the freeness test is at best imperfect.

Another disadvantage of the freeness test is that it more completely measures one of two important actions of the refining process, i.e., one of two separate actions on the fibers. The first action is external fibrillation which causes an increase in the concentration of fine particulate material, separating this from the fibers by abrasion. External fibrillation has an important effect on the quality of the paper, but is only of secondary value in developing good tensile strength properties. The second action is internal fibrillation to develop internal surface area, causing the fibers' internal bonds to be ruptured so that they become soft and swollen. The degree of internal fibrillation can be correlated with the increase in the specific volume of the fiber and improvement in the tensile strength properties of the paper. The freeness test in common use today is more a measure of external than internal fibrillation, and therefor is not an accurate measure of the more important pulp suspension qualities.

SUMMARY OF THE INVENTION

It is therefore an object of this invention to provide an apparatus and a method for measuring the quality of a pulp suspension which shows improved correlation between the quality of the paper and the degree of refining.

It is a further object of the present invention to provide a new apparatus and method to measure a quality of the pulp suspension which includes internal fibrillation and which utilizes the hydrodynamic properties of the fibers in the pulp suspension.

It is still a further object of the present invention to provide an improved apparatus and an improved method for determining the quality of a pulp suspension which is a function of refining and which correlates closely with the physical characteristics of the paper made from the refined pulp suspension.

In accordance with the present invention, a refined pulp suspension, of suitable consistency, is injected into the mixing chamber of the measuring device of this invention at a flow rate sufficiently high to generate enough turbulence for uniformly mixing the fibers in the suspension. The uniform mixed suspension is then passed from the mixing chamber into a settling chamber through a streamlined section interconnecting the chambers. The settling chamber includes one or more light sources for transmitting light beams horizontally through the pulp suspension to one or more detectors mounted on the opposite side for reception of the beams.

BRIEF DESCRIPTION OF THE DRAWINGS

FIG. 1 is a plan view, in cross-section, of the apparatus for measuring the degree of refining of pulp fibers, showing the enclosure as well as the light source and detectors;

FIG. 2 is a cross-sectional view taken along lines 2—2 of FIG. 1;

FIG. 3 is a cross-sectional view taken along lines 3—of FIG. 1;

FIG. 4 is a side view of the detector matrix taken along lines 4—4 of FIG. 1;

FIG. 5 is a graph showing the relationship between the height of the settling fiber-water interface with time; and FIG. 6 is a graph showing the relationship between the interface settling time and refining time.

DETAILED DESCRIPTION OF THE INVENTION

Referring now to FIGS. 1 to 3 of the drawings, there is shown the measuring apparatus 10 for determining the degree of refining of pulp fibers in accordance with the present invention. Apparatus 10 includes a hermetically sealable enclosure 12 which has a mixing chamber 14 and a settling chamber 16. Mixing chamber 14 is generally of square cross-sectional configuration along the direction of flow, as best seen in FIG. 3, and is provided with a plurality of inlet ports which are generally indicated by reference character 18. Settling chamber 16 is constructed to provide streamlined flow therethrough to prevent turbulence and is generally of rectangular cross-sectional configuration along the direction of flow, as best seen in FIG. 2. In accordance with a proposed embodiment of apparatus 10, the height of mixing chamber 14 and settling chamber 16 are the same, namely 6 inches, and the width of the two sections are, respectively, 6 inches and 4 inches, i.e., a ratio of 3 to 2. Settling chamber 16 is provided with a plurality of outlet ports which are generally indicated by reference character 20.

Settling chamber 16, as best seen in FIG. 3, includes two parallel vertical walls 22 and 24 which have at least a transparent portion to allow a light beam from a source 26 to be transmitted through the sample in the settling chamber to a detector matrix 28. Disposed between source 26 and vertical wall 22 is an infrared blocking filter which prevents any heat from light source 26 from reaching the interior of settling chamber 16, and a lens diagrammatically shown at 32 which will convert the diverging light from source 26 into a parallel or near parallel beam of light which passes through settling chamber 16 to detector matrix 28. Of course, it should be understood that filter 30 may be unnecessary if vertical wall 22 is constructed of an infrared filter material, or if the light source emits a negligible fraction of infrared radiation.

It should also be understood that the beam of light entering the measuring chamber need not necessarily be parallel. Divergent, convergent or diffusely transmitted light through the chamber may be and has been used successfully.

In operation, a sample of the pulp suspension from the refining station is removed and because such a sample has a normal consistency of approximately 2% to 3%, which means there are 2 to 3 parts of fibers to 100 parts of water by weight, it must be diluted because it has been found that fibers are better behaved at a somewhat lower consistency. A consistency which has been determined to be eminently suitable for the determination of the settling rate is in the range of between 0.02% and 0.2% which means between 2 and 20 parts of fibers to 10,000 parts of water by weight, with a consistency of 0.1% having been found most satisfactory. The pulp, after refining, is generally pressurized at 5 to 150 psi. This pressure is maintained through the dilution, mixing, flowing and settling operations, to inhibit the formation of air bubbles.

After the pulp suspension from the refining station is diluted to a consistency within the limits set forth above, it is injected into mixing chamber 14 through input ports 18. The turbulence generated by injecting the suspension assures thorough mixing in the mixing chamber of the fibers with the water before it flows through the streamlined flow section of the settling chamber, and out through outlet port 20 back into the pump to establish what is normally referred to as a closed system. After there is assurance that the fibers are uniformly distributed throughout the water, the flow of the suspension is stopped, by either closing the inlet and outlet ports or by shutting off the pump, to allow the sample to come to a standstill and the measurement of the settling rate to commence.

The light from light source 26, approximately collimated by lens 32, is transmitted through the now stationary pulp suspension and received by a detector matrix 28, such as the one shown in FIG. 4. Detector matrix 28 may comprise a number of light detectors such as the nine photocells respectively marked as 28A to 28I, each of which provides an electrical output signal which is related to the transmissivity of the pulp suspension. To perform a settling measurement, in accordance with the present invention, the output signals of any two vertically aligned detectors are monitored. As the interface between the fiber suspension and the clearer liquid descends past the two detectors, the incident optical intensity will rise sharply and the time at which this occured is recorded. The difference between the time when the intensity rises for two detectors, such as 28B and 28B, is the time it took the fiber-liquid interface to settle a distance corresponding to the separation of these two detectors, and this time has been found to furnish a reliable measure of the pulp suspension quality, as will now be explained.

Referring now to FIG. 5, there is shown a graph 50 which presents a plot of the change of the height of the interface between the fiber in the pulp suspension and the clearer water in the pulp suspension with time, the time being measured from the cessation of agitation. The term interface, as used herein, refers to the fiber-water interface which defines an abrupt discontinuity in the suspension. As is readily seen on graph 50, at the cessation of agitation, a small period of time elapses during which the interface becomes defined and slowly starts to move downwards, i.e., settles. After the interface becomes defined, it starts to settle initially at a fast rate and thereafter slows down to asymptotically approach the abscissa the curve being substantially exponential.

The slow down in settling time is readily explainable in terms of compaction, which means that the fiber interface encountered more resistance as it descends because of the rising fiber density underneath the interface. From graph 50 it can be seen that the rate during which the descent is fairly rapid is from the height marked $H_1$ to the height marked $H_2$, and since the entire height of the channel is indicated as $H_o$, the optimum placement of two detectors for the measurement of the interface descent rate would be at $H_1$ and $H_2$ for measurement convenience.

Referring now to FIG. 6, there is shown a graph 60 and a graph 62, both of which represent a plot of the interface settling time with pulp suspension refining time. It is clear from graphs 60 and 62 that the settling time increases with refining time and that, therefore, the settling time gives a measure of the refining time. It is also to be noted that different types of pulp suspension have different settling times, curve 60 representing softwood fibers and graph 62 representing hardwood fibers.

Even though the method of measuring the settling time of the fiber-water interface described above involved the utilization of two vertically aligned detectors, positioned to take advantage of the linear portion of the rate of descent curve, it is to be understood that there are other meaningful methods of measuring the descent rate of the fibers. For example, a single detector may be placed at a selected position, and the time may be measured from the instant of cessation to agitation to the time the interface reaches the sample detector. Furthermore, instead of utilizing one or two detectors, a plurality of vertically aligned detectors may be utilized to essentially obtain data in the form of a plurality of time intervals taken by the interface to traverse the plurality of intervals. The important aspect of this invention is the recognition that the beating time and the settling time are interrelated, and that therefore the settling time and the quality of the pulp suspension are interrelated. The settling time can be determined by measuring the hydrodynamic properties of the fiber and the velocity and the acceleration of the interface are measurements of such hydrodynamic properties.

Further, even though the method of practicing this invention has been described in connection with a pulp suspension, a sample that is initially operated in a closed loop for purposes of agitation and then is allowed to come to rest, there are other ways in which a uniform distribution of the fibers within the water can be assured. The important aspect of the method of this invention is to start the measurement of the hydrodynamic properties of the fibers with a pulp suspension sample having the fibers uniformly distributed therethrough.

What is claimed is:

1. The method of measuring the quality of a refined pulp suspension comprising the steps of:
    preparing a sample of the refined pulp suspension having a preselected consistency which is less than normal consistency;
    agitating the sample so that the fibers are uniformly distributed throughout the volume of the sample;
    discontinuing agitation to allow the fibers in the pulp suspension to settle;
    measuring a descent characteristic of the fiber-water interface in the pulp suspension; and
    using that descent characteristic to determine the quality of the pulp suspension.

2. The method of measuring the quality of a refined pulp suspension in accordance with claim 1 in which the consistency of said sample is selected between 2 and 20 parts of fiber per 10,000 parts of water by weight.

3. The method of measuring the quality of a refined pulp suspension in accordance with claim 1 in which the consistency of said sample is selected between 8 to 12 parts of fibers per 10,000 parts of water by weight.

4. The method of measuring the quality of a refined pulp suspension in accordance with claim 1 in which the descent is measured by optically determining the passage of the fiber-water interface past two vertically spaced apart levels and the time elapsed between passages.

5. The method of measuring the quality of a refined pulp suspension in accordance with claim 4 in which the position of the lower of said two levels is selected in accordance with the consistency of the pulp suspension.

6. The method of measuring the quality of a refined pulp suspension in accordance with claim 1 in which said pulp suspension sample is pressurized to inhibit the formation of air bubbles.

7. The method of measuring the quality of a refined pulp suspension in accordance with claim 1 in which said pulp suspension sample is pressurized at a pressure selected between 5 and 150 pounds per square inch.

8. An apparatus for the measurement of the quality of a refined pulp suspension comprising:
    a chamber including a mixing section having an inlet port and a settling section having an outlet port, said settling section being shaped to provide a streamlined flow therethrough;
    means for injecting the pulp suspension into said mixing section through said inlet port for intermixing said pulp suspension such that the concentration of said pulp suspension becomes substantially uniform throughout as it flows through said settling section and out of said outlet port;
    means for stopping the flow of the pulp suspension through said chamber to allow the suspension to become stationary and the fibers therein to form a fiber-water interface; and
    means disposed proximate to said settling section for optically determining the fiber-water interface descent in the pulp suspension.

9. An apparatus for the measurement of the quality of a refined pulp suspension in accordance with claim 8 in which said means for determining the interface descent includes means for determining the passage of the fiber-water interface across at least two vertically spaced apart levels.

10. An apparatus for the measurement of the quality of refined pulp suspension in accordance with claim 8 in which said means for determining the fiber-water interface descent includes means for measuring its vertical rate of change of position.

11. An apparatus for the measurement of the quality of refined pulp suspension in accordance with claim 8 in which said chamber is pressurized to inhibit the formation of air bubbles.

* * * * *